United States Patent [19]

Hasegawa

[11] 4,265,622

[45] May 5, 1981

[54] FOOT CONTROLLER FOR ELECTRICAL DENTAL INSTRUMENTS

[75] Inventor: Hiroshi Hasegawa, Tokyo, Japan

[73] Assignee: Tokyo Engine Kogyo Kabushiki Kaisha, Tokyo, Japan

[21] Appl. No.: 38,003

[22] Filed: May 11, 1979

[30] Foreign Application Priority Data

May 17, 1978 [JP] Japan .............................. 53-66299[U]

[51] Int. Cl.³ .............................................. A61C 1/02
[52] U.S. Cl. .................................................. 433/101
[58] Field of Search ........................................ 433/101

[56] References Cited

U.S. PATENT DOCUMENTS

| 493,431 | 3/1893 | Keller .................................... 433/101 |
| 3,411,209 | 11/1968 | Stemler et al. ....................... 433/101 |

FOREIGN PATENT DOCUMENTS

| 2752713 | 6/1978 | Fed. Rep. of Germany ........... 433/101 |
| 2725144 | 12/1978 | Fed. Rep. of Germany ........... 433/101 |

Primary Examiner—Gene Mancene
Assistant Examiner—John J. Wilson
Attorney, Agent, or Firm—Fred Philpitt

[57] ABSTRACT

A roller is installed in a case having an opening at its upper cover, in such a manner that the outer marginal portion of the roller projects partially through the opening of the case. No return force is applied to the roller at all and the same can be rotated by a foot of a dentist. A variable resistor adapted to transmit the turning movement of such roller is also installed in the case so that the change in resistance occurs in proportion to the turning movement of the roller. A cord of the variable resistor extends out of the case and the forward end of such cord is fitted with a plug.

1 Claim, 7 Drawing Figures

FOOT CONTROLLER FOR ELECTRICAL DENTAL INSTRUMENTS

BACKGROUND OF THE INVENTION

Among various conventional instruments for dental treatment, there are known a handengine, a handpiece or the like which require motive power to be provided by a motor. Such dental treatment instruments as a handengine, a handpiece or the like should be of course controlled to run at a rate suitable for a diseased part or parts of the teeth to be treated. A conventional controller to adjust the running rate of the handpiece or the handengine is designed to be manipulated by a foot of a dentist. More specifically, shown in FIGS. 6 and 7 annexed to this specification are commonly known typical foot controllers, wherein a foot controller designated generally by reference numeral 30 in FIG. 6 is of the construction to be operated by causing a lever 31 to slide horizontally with the dentist's foot thereby to control the variable resistor (not shown) installed within the controller in order to adjust the running rate of the handengine or the handpiece, whilst a foot controller designated generally by reference numeral 40 being of the construction to be operated by stepping on the cover 41 thereby to actuate the variable resistor (not shown) installed within the controller in order to adjust the running rate of the handpiece or the handengine. Either of the lever 31 or the cover 41 of the aforementioned conventional controllers 30, 40 is designed to return to its original position by means of a coiled spring. It will therefore be necessary for a dentist to see that his foot be always in touch with the lever 31 or with the cover 41 in order to control the dental engine or the handengine at a proper running velocity. This will apparently be a tiresome work for a dentist, as he will have to always be careful in keeping his foot in touch with the lever or the cover of the controller during medical treatment. Nervous fatigue will be unavoidable. Physical fatigue will also be unavoidable due to nervous footwork required during medical treatment.

BRIEF SUMMARY OF THE INVENTION

This invention relates to a foot controller having no such defects as are seen in the prior art controllers referred to above, the foot controller according to the present invention being of the type to allow a dentist, in the first place, to adjust the running velocity at a required rate and then to give his close attention entirely to the medical treatment without paying any further or additional nervous attention to the foot controller.

In order to provide such type of foot controller, a roller which is to act in lieu of the lever or the cover in the prior foot controllers as discussed above is installed in a case having an opening at its upper cover, in such a manner that the outer marginal portion of the roller projects out of the case partially through the opening of the case so that the projected marginal portion of the roller may be caused to rotate by a foot of a dentist. With the rotation of the roller, change in the resistance of a variable resistor which is also installed within the case occurs correspondingly. The roller is not provided with any return force at all, which is one of the characteristic features of the present invention.

Additional characteristic feature of the present invention resides in the provision of a foot controller with concise construction wherein the aforementioned roller represents a hollow disk having at its outer periphery a flange such that a gear and a pinion which are to transmit the turning movement of the roller to the variable resistor are disposed within the hollow space defined by the disk and the flange.

BRIEF DESCRIPTION OF THE DRAWINGS

How the foregoing advantages are attained will appear more fully from the following description referring to the accompanying drawings, in which.

DETAILED DESCRIPTION OF THE INVENTION

Figure 1:
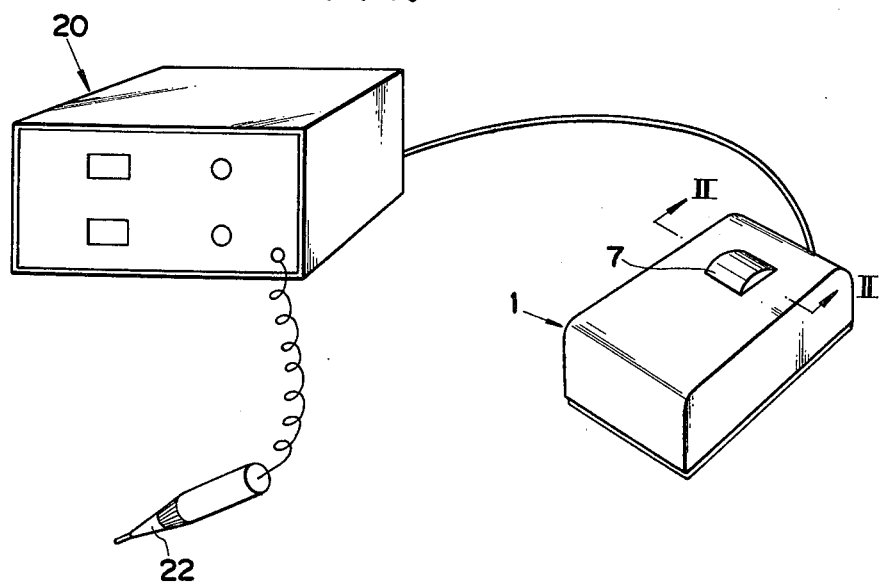
FIG. 1 is a generic view of a foot controller according to the present invention, showing actual use thereof in combination with a handengine.

Referring now to the drawings, designated generally by reference numeral 1 is a foot controller according to the present invention.

The foot controller 1 consists generally of a body 2a and a cover 2b. The cover 2b is provided with an opening 3 at its top portion. Provided horizontally within the body 2a and designated by reference numeral 6 is a rotor shaft, both ends being supported by bearing 4 and 5. Designated by reference numeral 7 is a roller which is fixed to the rotor shaft 6 by means of a screw 8. No coiled spring or the like which will give the roller 7 a return force is provided at all. The roller 7 is installed within the body 2a in such a manner that the outer marginal portion of the roller projects partially through the opening 3 formed in the cover 2b.

Figure 2:
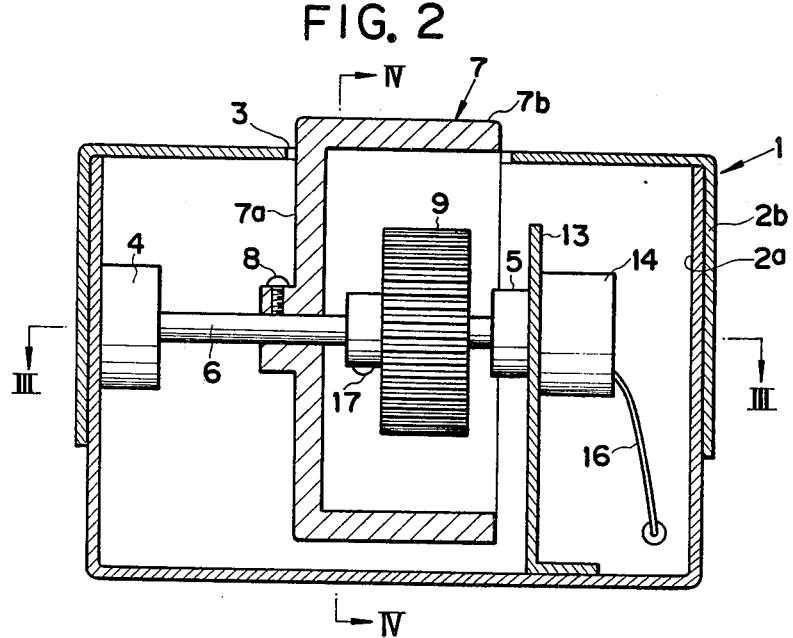
FIG. 2 is a longitudinal section taken along the lines II—II of FIG. 1.
Figure 3:
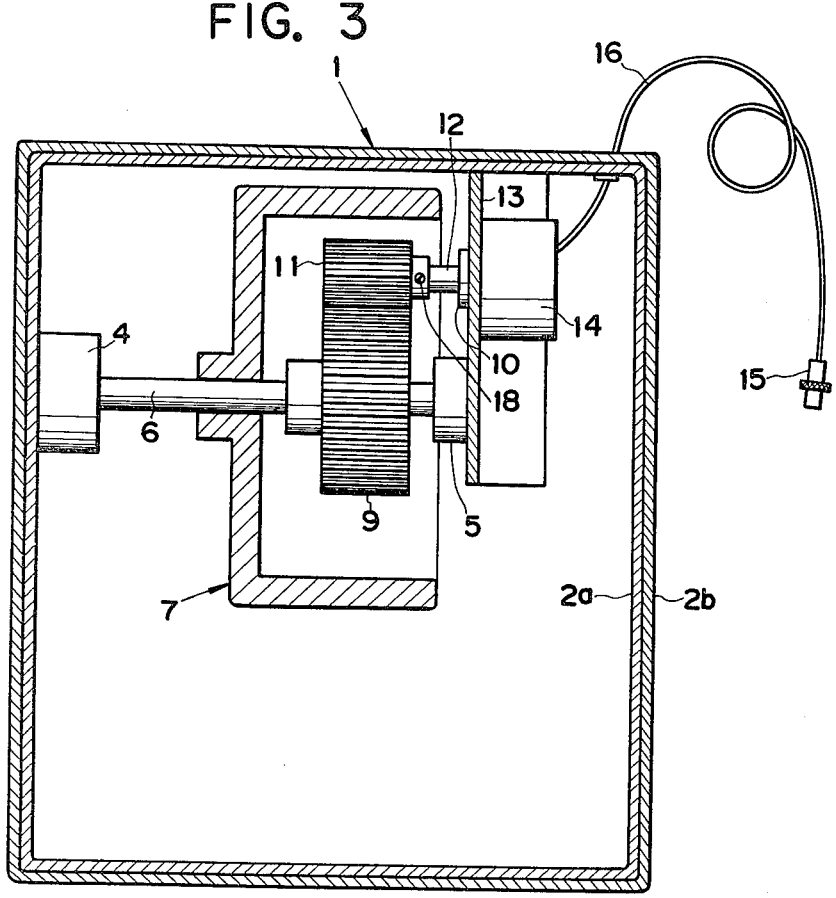
FIG. 3 is a transverse section taken along the lines III—III of FIG. 2.
Figure 4:
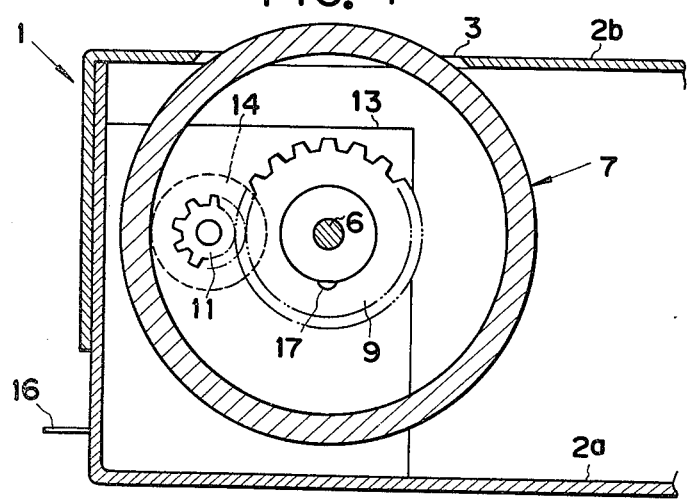
FIG. 4 is a longitudinal section taken along the lines IV—IV of FIG. 2.

The roller 7 consists of a disk 7a and a cylindrical flange 7b extending along the outer periphery of the disk 7a, representing in combination a one-side open hollow construction, as will best be seen in FIG. 2. A gear 9 is disposed within the hollow space of the roller 7 and is fixed to the rotor shaft 6 by means of a screw 17. The gear 9 is arranged to be in a position to engage with a pinion 11 which is fixed to a rotor shaft 12 of a rotary variable resistor 14 by means of a screw 18, as can be seen in FIG. 3. In this way, the gear 9 and the pinion 11 are compactly housed by the hollow space of the roller 7. The variable resistor 14 is fixed to a supporting plate 13 extending from the wall of the body case 2a. A cord 16 of the variable resistor 14 extends out of the controller case and the forward end of such cord 16 is fitted with a plug designated by reference numeral 15.

Figure 5:
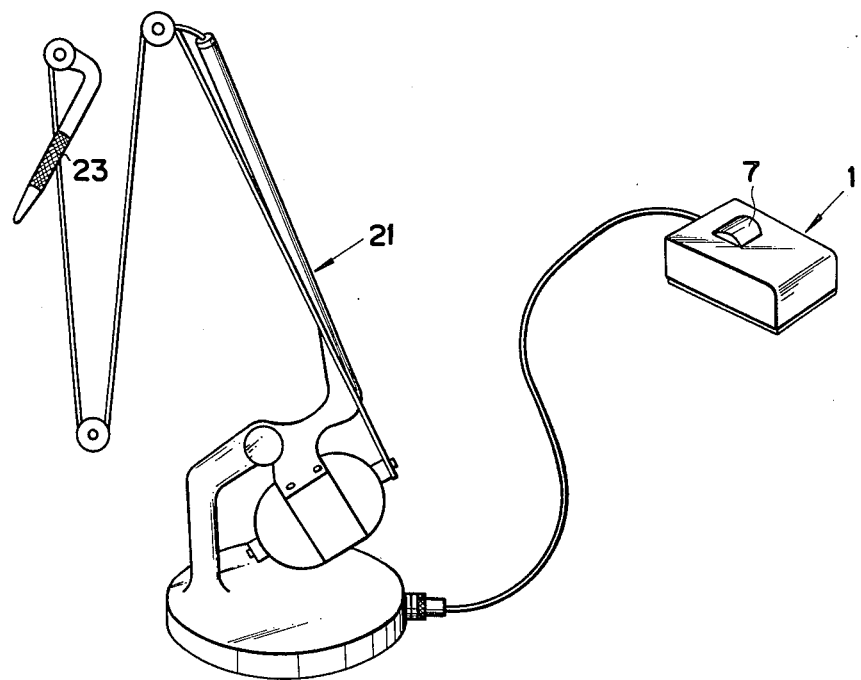
FIG. 5 is a perspective view of a foot controller according to the present invention, showing actual use thereof in combination with a dentalengine.
Figure 6:
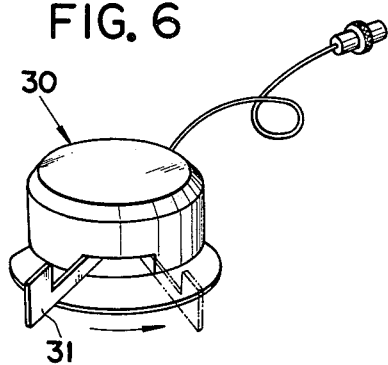
FIG. 6 is a perspective view of a conventional lever-type foot controller.
Figure 7:
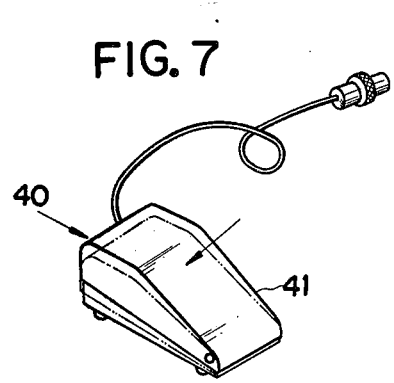
FIG. 7 is a perspective view of a conventional treadle-type foot controller.

In an actual application of the foot controller according to the present invention, the foot controller 1 is disposed on the floor in the first place and the plug 15 of the cord 16 will be connected to a control box 20 for a handengine 22 as shown in FIG. 1 or connected to a dental engine 21 for a handpiece 23 as shown in FIG. 5, whereafter the roller 7 protruding partially through the opening 3 of the case cover 2b will be rotated with a dentist's foot, forward or backward, to thereby cause the rotor member (not shown) of the variable resistor 14 to be rotated in order to adjust the handengine or the handpiece to run at a rate suitable for a diseased part or parts of the teeth to be treated.

Since the roller 7 of the foot controller according to the present invention is given no return force by a coiled spring or the like at all, there will be no necessity of a dentist to always be careful in keeping his foot in touch with the roller, once the running velocity of the handengine or handpiece has been set at a required rate through the rotation of the roller 7. The foot controller according to the present invention will allow a dentist to give his close attention entirely to the medical treatment without paying any nervous attention to the foot controller as in the case of the conventional foot controllers.

Additional advantage of the present invention will reside in the provision of a foot controller with concise construction as discussed above in connection with the preferred embodiment, wherein the roller 7 represents a one-side open hollow construction to accommodate therein the gear 9 and the pinion 11.

While there has been described what is at present to be the preferred embodiment of the present invention, it will be understood that various modifications may be made therein, and it is intended to cover in the appended claims all such modifications as fall within the true spirit and scope of the present invention.

What is claimed is:

1. A foot controller for electrical dental instruments, comprising in combination: a case consisting of a body and a cover having at its upper portion an opening; a rotor shaft having no self returning force at all and supported within said case horizontally by means of a bearing member; a roller having a disk fixed to said rotor shaft and a flange extending along the outer periphery of said disk, an upper portion of said outer periphery of said flange protruding through said opening of said cover; a gear installed in a space defined by said disk and said flange of said roller; a rotary variable resistor installed in said case; a pinion fixed to a rotor shaft of said variable resistor and installed in a position to engage with said gear in said space defined by said disk and said flange of said roller; and a cord connected to said variable resistor and having at its forward end a plug.

* * * * *